(12) United States Patent
Zakharenko

(10) Patent No.: US 8,895,511 B2
(45) Date of Patent: Nov. 25, 2014

(54) USE OF SARCOPLASMIC $CA^{2+}$-ATPASE TYPE 2 PROTEIN FOR DIAGNOSING AND TREATING LEARNING OR MENTAL DISORDERS

(75) Inventor: Stanislav S. Zakharenko, Collierville, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 13/511,388

(22) PCT Filed: Nov. 16, 2010

(86) PCT No.: PCT/US2010/056778
§ 371 (c)(1),
(2), (4) Date: May 23, 2012

(87) PCT Pub. No.: WO2011/066132
PCT Pub. Date: Jun. 3, 2011

(65) Prior Publication Data
US 2012/0232121 A1    Sep. 13, 2012

Related U.S. Application Data

(60) Provisional application No. 61/263,872, filed on Nov. 24, 2009.

(51) Int. Cl.
*A01N 61/00* (2006.01)
*A61K 31/00* (2006.01)
*C12Q 1/68* (2006.01)
*G01N 33/68* (2006.01)

(52) U.S. Cl.
CPC ........ *C12Q 1/6883* (2013.01); *C12Q 2600/158* (2013.01); *G01N 2800/28* (2013.01); *G01N 2333/91205* (2013.01); *G01N 33/6896* (2013.01); *G01N 33/6893* (2013.01); *C12Q 2600/136* (2013.01)
USPC ........................................ 514/17.5; 514/17.7

(58) Field of Classification Search
None
See application file for complete search history.

(56) References Cited

U.S. PATENT DOCUMENTS

| 2003/0044776 A1 * | 3/2003 | Dykens et al. | 435/6 |
| 2005/0239110 A1 | 10/2005 | Rokutan et al. | 435/6.16 |
| 2007/0134664 A1 | 6/2007 | Hager et al. | 435/6.16 |
| 2009/0258794 A1 | 10/2009 | Chaudhuri | 506/10 |

OTHER PUBLICATIONS

Behnisch, T. and Reymann, K. G. "Thapsigargin Blocks Long-term Potentiation Induced by Weak, But Not Strong Tetanisation in Rat Hippocampal CA1 Neurons" Neuroscience Letters 1995 192:185-188.
Jurata et al. "Altered Expression of Hippocampal Dentate Granule Neuron Genes in a Mouse Model of Human 22q11 Deletion Syndrome" Schizophrenia Research 2006 88:251-259.
Luo et al. "Targeted Ablation of the Phospholamban Gene is Associated with Markedly Enhanced Myocardial Contractility and Loss of β-Agonist Stimulation" Circulation Research 1994 75(3):401-409.
Matias et al. "Thapsigargin Blocks STP and LTP Related Calcium Enhancements in Hippocampal CAI Area" NeuroReport 2002 13(18):2577-2580.
Prescott et al. "Microarray Analysis of the *Df1* Mouse Model of the 22q11 Deletion Syndrome" Human Genetics 2005 116:486-496.
Ruiz-Perez et al. "*ATP2A2* Mutations in Darier's Disease: Variant Cutaneous Phenotypes are Associated with Missense Mutations, but Neuropsychiatric Features are Independent of Mutation Class" Human Molecular Genetics 1999 vol. 8(9):1621-1630.
Stark et al. "Altered Brain MicroRNA Biogenesis Contributes to Phenotypic Deficits in a 22q11-Deletion Mouse Model" Nature Genetics 2008 40(6):751-760.
Zhang et al. "Presenilins are Essential for Regulating Neurotransmitter Release" Nature 2009 460:632-636.
International Search Report from PCT/US2010/056778, Mar. 22, 2011, PCT.
International Preliminary Report on Patentability from PCT/US2010/056778, May 30, 2012, PCT.

* cited by examiner

*Primary Examiner* — Olga N Chernyshev
(74) *Attorney, Agent, or Firm* — Licata & Tyrell P.C.

(57) ABSTRACT

The present invention embraces methods for the diagnosis and treatment of learning or mental disorders, as well as the identification of agents useful in the treatment of such disorders based upon the identified involvement of Sarcoplasmic $Ca^{2+}$-ATPase type 2 Protein in synaptic plasticity and neurotransmitter release in 22q11 deletion/DiGeorge Syndrome.

1 Claim, No Drawings

USE OF SARCOPLASMIC $CA^{2+}$-ATPASE TYPE 2 PROTEIN FOR DIAGNOSING AND TREATING LEARNING OR MENTAL DISORDERS

INTRODUCTION

This application is a U.S. National Stage Application of PCT/US2010/056778 filed Nov. 16, 2010 and claims benefit of priority to U.S. Provisional Application Ser. No. 61/263,872 filed Nov. 23, 2009, the contents of each of which are incorporated herein by reference in their entirety.

This invention was made in the course of research sponsored by the National Institute of Mental Health, grant number R01MH079079. The U.S. government has certain rights in this invention.

BACKGROUND OF THE INVENTION

The most common microdeletion syndrome is 22q11 deletion syndrome (22q11DS), also known as velocardiofacial syndrome or DiGeorge syndrome, which occurs in approximately 1 in every 4000 live births (Oskarsdottir, et al. (2004) *Arch. Dis. Child* 89:148-151). The syndrome is caused by a hemizygous deletion of a 1.5- to 3-megabase region within 22q11.2 that occurs either sporadically (85%-95% of cases) or as an inherited autosomal-dominant trait (5%-15% of cases) (Swillen, et al. (1998) *Am. J. Med. Genet.* 80:531-532). Cognitive defects occur in virtually all patients with 22q11DS. Children with 22q11.2DS have a high incidence of mild to moderate mental retardation and characteristic learning disabilities (Bearden, et al. (2001) *J. Clin. Exp. Neuropsychol.* 23:447-464; Eliez, et al. (2000) *Eur. Child Adolesc. Psychiatry* 9:109-114; Swillen, et al. (2000) *Am. J. Med. Genet.* 97:128-135). In approximately 30% of them schizophrenia or schizoaffective disorder develops during adolescence or early adulthood (Chow, et al. (2006) *Schizophr. Res.* 87:270-278; Pulver, et al. (1994) *J. Nerv. Ment. Dis.* 182:476-478).

The orthologous region of the human 22q11.2 locus lies on mouse chromosome 16. With one exception, all of the human genes in this region are represented in the mouse, although organized in a different order (Puech, et al. (1997) *Proc. Natl. Acad. Sci. USA* 94:14608-14613). Generation of mouse models that carry chromosomal deficiencies that are syntenic to the human 22q11.2 microdeletion have been reported (Lindsay, et al. (1999) *Nature* 401:379-383; Stark, et al. (2008) *Nat. Genet* 40:751-760; Merscher, et al. (2001) *Cell* 104:619-629).

Cognitive defects were demonstrated through the conditioned contextual fear paradigm in mouse models of 22q11.2DS (Df(16)1/+ mice) (Paylor, et al. (2001) *Hum. Mol. Genet.* 10:2645-2650), suggesting that hippocampal function is impaired by 22q11.2DS. Recent data support this idea by showing abnormal development of dendrites and dendritic spines in the hippocampal pyramidal neurons of another mouse model of 22811.2 DS (Mukai, et al. (2008) *Nat. Neurosci.* 11:1302-1310). Several reports have indicated that the gross morphology of the hippocampus is also affected in patients with 22q11.2DS (Chow, et al. (2002) *Biol. Psychiatry* 51:208-215; Debbane, et al. (2006) *Neuropsychologia* 44:2360-2365; Deboer, et al. (2007) *Behav. Brain Funct.* 3:54; Eliez, et al. (2001) *Am. J. Psychiatry* 158:447-453), and this observation positively correlates with the occurrence of cognitive impairment (Deboer, et al. (2007) supra).

Although these behavioral and morphological data point to the hippocampus as a brain region affected during 22q11DS, little is known about the consequences of 22q11.2 microdeletions on hippocampal synaptic plasticity, the activity-dependent changes in synaptic efficacy, such as long-term potentiation (LTP) and long-term depression (LTD) that are believed to be important for information storage, fine-tuning of synaptic connections, and learning and memory (Martin, et al. (2000) *Annu. Rev. Neurosci.* 23:649-711; Milner, et al. (1998) *Neuron* 20:445-68). Moreover, it is not known whether changes in synaptic plasticity and behavior progress with age in a manner similar to the progression of symptoms in patients with 22q11.2DS. More importantly, nothing is known about the molecular mechanisms that are involved in synaptic plasticity and are affected by 22q11.2 microdeletions.

SUMMARY OF THE INVENTION

The present invention features a method for identifying an agent useful for the treatment of a mental disorder by contacting SERCA2 protein or nucleic acids encoding the same with a candidate agent and determining whether the candidate agent inhibits SERCA2 expression or activity.

The present invention also features a method for treating a learning disorder or mental disorder by administering to a subject in need of treatment a therapeutically effective amount of a SERCA inhibitor. In one embodiment, the SERCA inhibitor is selected from the group consisting of cyclopiazonic acid, thapsigargin and a thapsigargin prodrug. In other embodiments, the mental disorder is a psychiatric disease such as schizophrenia, Alzheimer's disease, bipolar disorder, schizoaffective disorder, DiGeorge syndrome, attention-deficit hyperactivity disorder, obsessive-compulsive disorder or autism spectrum disorder.

An additional feature of this invention is a method for diagnosing the susceptibility for developing a learning or mental disorder by obtaining a biological sample from a subject, and measuring the level of SERCA2 protein or activity in said sample, wherein an elevated level of SERCA2 protein or activity as compared to a control indicates an increased susceptibility to developing a learning or mental disorder. In some embodiments, the mental disorder is a psychiatric disease such as schizophrenia, Alzheimer's disease, bipolar disorder, schizoaffective disorder, DiGeorge syndrome, attention-deficit hyperactivity disorder, obsessive-compulsive or autism spectrum disorder. In other embodiments, the level of SERCA2 is measured by protein analysis or enzymatic analysis.

In addition to the use of SERCA2, the present invention also features a method for diagnosing a subject suspected of having a learning or mental disorder by measuring the level of synaptic activity of the subject, wherein an elevated level of neurotransmitter released from presynaptic terminals as compared to a control subject is indicative of a learning or mental disorder.

DETAILED DESCRIPTION OF THE INVENTION

22q11 deletion syndrome (22q11DS) is marked early in life by cognitive deficits, which are compounded during maturation by an increased risk for development of psychiatric disease, most commonly schizophrenia. Molecular mechanisms of neuronal dysfunction in 22q11DS have now been identified using a mouse model of 22q11DS (Df(16)1/+ mice) that shows mild functional phenotypes early on, but develops a substantial enhancement in short- and long-term synaptic plasticity at the hippocampal CA3-CA1 synapse, which coincides with deficits in hippocampus-dependent spatial memory. These changes are evident in mature but not young animals. Electrophysiological, two-photon imaging and glutamate uncaging, and electron microscopic assays in acute brain slices showed that enhanced neurotransmitter release but not altered postsynaptic function or structure caused these changes. Enhanced neurotransmitter release in Df(16)1/+ mice coincided with altered calcium kinetics in CA3 presynaptic terminals and upregulated sarco(endo)plasmic reticulum calcium-ATPase type 2 (SERCA2). SERCA inhibitors rescued synaptic phenotypes of Df(16)1/+ mice. These results indicate that presynaptic SERCA2 upregulation is a pathogenic event contributing to cognitive and psychiatric symptoms of 22q11DS such that inhibition of SERCA2 finds application in alleviating the cognitive symptoms of 22q11DS and schizophrenia, as well as other learning or mental disorders. Accordingly, the present invention embraces a method for identifying an agent useful for the treatment of a mental disorder and methods for treatment and diagnosis of learning or mental disorders using SERCA2 as a target.

For the purposes of the present invention, a SERCA2 protein, also known as ATPase, Ca(2+)-Transporting, Slow-Twitch (ATP2A2), is intended to mean a SERCA2 protein from mammals such as mice, rat, bovine, dog or, most desirably, human. These proteins are known in the art and their sequences are readily available under GENBANK Accession Nos. NP_733765 (human), NP_001003214 (dog), XP_612129 (bovine), NP_033852 (mouse), and NP_058986 (rat), which are incorporated by reference as of the date of filing.

In accordance with the instant screening assay, a SERCA2 protein or nucleic acid encoding the same (e.g., in a cell) is contacted with a candidate agent and it is determined whether the candidate agent inhibits SERCA2 expression or activity, wherein a candidate agent that inhibits SERCA2 expression or activity is indicative of an agent useful in the treatment of a mental disorder. According to the instant screening assay, changes in SERCA2 expression or activity can be determined biochemically (e.g., an enzyme kinetic assay), in an assay measuring the expression level of SERCA2 (protein levels), in an assay measuring physiological characteristics of a cell (e.g., intracellular $Ca^{2+}$ levels) and/or in an assay monitoring changes in behavior of a mammal. As used herein, "contacting" has its normal meaning and refers to combining two or more entities (e.g., a protein and a candidate agent, a polynucleotide and a cell, a cell and a candidate agent, etc.). Contacting can occur in vitro (e.g., a candidate agent and a cell lysate or isolated SERCA2 protein are combined in a test tube or other container) or in vivo (e.g., a candidate agent and an intact test cell are combined in a container or an animal model is administered the candidate agent).

An agent that inhibits SERCA2 activity is an agent that binds to the SERCA2 protein or nucleic acids encoding SERCA2 and reduces, blocks, or inhibits its expression and/or ability to pump calcium. Agents that can be assayed in the instant screening method include any substance, molecule, element, compound, entity, or a combination thereof. It includes, but is not limited to, e.g., proteins (including antibodies), oligopeptides, small organic molecules, polysaccharides, polynucleotides (e.g., DNA or RNA, including polynucleotides encoding a gene product of interest, or which act as a cell modulator without transcription or without translation), and the like. It can be a natural product, a synthetic compound, or a chemical compound, or a combination of two or more substances. In so far as cyclopiazonic acid, thapsigargin and thapsigargin prodrugs are known in the art to possess SERCA inhibitory activity, particular embodiments of this invention encompass screening analogs of cyclopiazonic acid and thapsigargin for inhibitory activity. The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific isoform, or higher selectivity at a targeted isoform and lower activity levels at other isoforms) is an approach that is well-known in pharmaceutical chemistry. In this respect, particular embodiments of the present invention embrace an agent that has higher potency and/or higher selectivity for SERCA2, with limited or no inhibitory activity toward SERCA1 and/or SERCA3.

As indicated, SERCA2 activity can be assessed in vitro or in vivo. By way of illustration, inhibitory activity of a candidate agent can be assessed by measuring changes in the expression of SERCA2 protein levels. Detection of SERCA2 protein levels can be achieved with routine methods. For example, the detection (measurement) of SERCA2 protein levels can be carried out by using a compound that specifically binds to SERCA2 protein. The detection method (or measurement) is not particularly limited to this alone. However, the detection (measurement) is desirably carried out by an immunological technique. In immunological techniques, an antibody against the SERCA2 is used, and the protein is detected by using a binding property (binding amount) of the antibody as an indicator. The term used herein "antibody" includes a polyclonal antibody, a monoclonal antibody, a chimeric antibody, a single strand antibody, a CDR graft antibody, a humanized antibody, or the fragment thereof, and the like. The antibody of the present invention can be prepared by using an immunological technique, a phage display method, a ribosome display method, and the like. Examples of the immunological detection techniques include an ELISA method, radioimmunoassay, FACS, an immunoprecipitation method, immunoblotting, and the like.

By way of further illustration, an in vivo assay includes monitoring changes in intracellular calcium levels. In general, a calcium-based screen includes contacting the cells of interest with a candidate agent for a period of time sufficient for the agent to have an effect in the cell followed by measuring the calcium levels in the cells and assessing changes in calcium levels in the cell compared to, e.g., a cell not contacted with the agent. The time sufficient for the agent to have an effect will depend on the agent(s) being screened, where the contacting step may take from hours to days (e.g., approximately 1 hour for small molecule candidate agents, 2 days for siRNA candidate agents). Measuring the calcium levels can be achieved using any convenient method, including loading the cells with a calcium dye (e.g., Fura-2) or by employing cells expressing a fluorescent protein calcium indicator (e.g., cameleon). Once calcium levels in the cells are measured and assessed, agents that intracellular deplete calcium stores are identified as inhibitors of SERCA2 activity. Cells used in such screening assays can be any mammalian cell, including primary cells, transformed cells, genetically modified cells, etc. In certain embodiments, the cells are human cells (e.g., HeLa cells). The origin of cells is not particularly limited. However, it is preferable to use cells derived from the central nervous system tissue. Among the central nervous system tissue, it is preferable to use cells derived from the prefrontal cortex of the forebrain, the nucleus accumbens, the striatum, the midbrain, or the hippocampus.

Agents identified in the instant screening assay as inhibiting SERCA2 activity find use in the study of SERCA2 activity as well as in the prevention or treatment of diseases or conditions in which SERCA2 activity is implicated. In this respect, agents identified in the instant screening assay can be formulated in pharmaceutical compositions suitable for administration to a subject in need of treatment. Such compositions typically contain from about 0.1 to 90% by weight (such as 1 to 20% or 1 to 10%) of the SERCA2 inhibitor in a pharmaceutically acceptable carrier. A pharmaceutically acceptable carrier is a material useful for the purpose of administering the medicament, which is preferably sterile and non-toxic, and can be solid, liquid, or gaseous materials, which is otherwise inert and medically acceptable, and is compatible with the active ingredients. A generally recognized compendium of methods and ingredients of pharmaceutical compositions is Remington: The Science and Practice of Pharmacy, Alfonso R. Gennaro, editor, 20th ed. Lippincott Williams & Wilkins: Philadelphia, Pa., 2000.

The pharmaceutical compositions can be administered to the subject being treated by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, or long-term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the subject to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active agent(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

As indicated, SERCA inhibitors find application in the treatment or learning or mental disorders. In this respect, the present invention also embraces a method for treating a learning disorder or mental disorder by administering to a subject with a learning disorder or mental disorder a therapeutically effective amount of a SERCA inhibitor. As used herein, "treating" or "treatment" of a disease refers to arresting, ameliorating or delaying the onset of a disease, disorder, or at least one clinical symptom or physical parameter of a disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. Effectiveness of the a SERCA inhibitor can be determined by measuring or monitoring SERCA expression or activity.

Subjects benefiting from treatment in accordance with the instant method include those having, those suspected of having or those predisposed to have (e.g., genetic predisposition) a learning disorder or mental disorder. Learning disorders include childhood learning disorders, wherein the subject has an impaired ability to learn. Such learning disorders can be diagnosed by using the DSM-IV criteria (APA, 1994, Diagnostic and Statistical Manual of Mental Disorders (Fourth Edition), Washington, D.C.). Mental disorders embraced by the present invention include, but are not limited to psychiatric diseases such as schizophrenia, Alzheimer's disease, bipolar disorder, schizoaffective disorder, DiGeorge syndrome, attention-deficit hyperactivity disorder, obsessive-compulsive disorder and autism spectrum disorder.

As used herein, the term "schizophrenia" refers to a psychiatric disorder that includes at least two of the following: delusions, hallucinations, disorganized speech, grossly disorganized or catatonic behavior, or negative symptoms. Subjects can be diagnosed as schizophrenic using the DSM-IV criteria.

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann, et al. (1984) *Neurology* 34:939-944). The patient's cognitive function can be assessed by the Alzheimer's Disease Assessment Scale-cognitive subscale (ADAS-cog; Rosen, et al. (1984) *Am. J. Psychiatry* 141:1356-1364).

Bipolar disorder, also known as manic depressive disorder, manic depression or bipolar affective disorder, is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. Subjects can be diagnosed as having bipolar disorder using the DSM-IV-TR criteria and the World Health Organization's International Statistical Classification of Diseases and Related Health Problems, the ICD-10.

Schizoaffective disorder is a psychiatric diagnosis that describes a mental disorder characterized by recurring episodes of mood disorder and psychosis. Distortions in perception alternate with and occur simultaneously with elevated or depressed mood. These perceptual distortions may affect all five senses, including sight, hearing, taste, smell and touch, but most commonly manifest as auditory hallucinations, paranoid or bizarre delusions, or disorganized speech and thinking with significant social or occupational dysfunction. Subjects can be diagnosed as having a schizoaffective disorder using the DSM-IV-TR criteria.

Characteristic signs and symptoms of DiGeorge syndrome may include birth defects such as congenital heart disease, defects in the palate, most commonly related to neuromuscular problems with closure (velo-pharyngeal insufficiency), learning disabilities, mild differences in facial features, and recurrent infections. DiGeorge syndrome may be first spotted when an affected newborn has heart defects or convulsions from hypocalcemia due to malfunctioning the parathyroid glands and low levels of parathyroid hormone (parathormone). Affected individuals may also have any other kind of birth defect including kidney abnormalities and significant feeding difficulties as babies. Autoimmune disorders such as hypothyroidism and hypoparathyroidism or thrombocytopenia (low platelet levels), and psychiatric illnesses are common late-occurring features.

The term "attention-deficit hyperactivity disorder attention deficit disorder," as used herein, refers to a disorder that is most commonly exhibited by children and which can be characterized by increased motor activity and a decreased attention span. The DSM-IV criteria can be used to diagnose attention deficit disorder.

Obsessive-compulsive disorder (OCD) is a mental disorder characterized by intrusive thoughts that produce anxiety, by repetitive behaviors aimed at reducing anxiety, or by combinations of such thoughts (obsessions) and behaviors (compulsions). The symptoms of this anxiety disorder range from repetitive hand-washing and extensive hoarding to preoccupation with sexual, religious, or aggressive impulses as well as corrections of minor things. These symptoms can be alienating and time-consuming, and often cause severe emotional and economic loss. Although the acts of those who have OCD may appear paranoid and come across to others as psychotic, OCD sufferers often recognize their thoughts and subsequent actions as irrational, and they may become further distressed by this realization.

As used herein, the term "autism spectrum disorder" refers to a spectrum of psychological conditions characterized by widespread abnormalities of social interactions and communication, as well as severely restricted interests and highly repetitive behavior. Subjects with autism experience mental introversion characterized by morbid self-absorption, social failure, language delay, and stereotyped behavior. The three main forms of ASD are Autism, Asperger syndrome, Pervasive Developmental Disorder Not Otherwise Specified (PDD-NOS), sometimes called atypical autism. Patients can be diagnosed as suffering from autism by using the DSM-IV criteria.

Subjects to be treated in accordance with the instant method can be provided with a therapeutically effective amount of a SERCA inhibitor identified by the instant screening assay or agents known in the art to exhibit SERCA inhibitory activity. For example, cyclopiazonic acid, thapsigargin and thapsigargin prodrugs have been shown to inhibit SERCA activity. In addition, phospholamban is a known, endogenous, muscle-specific SERCA2 inhibitor (Luo, et al. (1994) Circ. Res. 75(3):401-409. Accordingly, analogs and prodrugs of these agents are embraced by the instant method. In some embodiments, the agent selected for treatment has a higher potency and/or higher selectivity for SERCA2, with limited or no inhibitory activity toward SERCA1 and/or SERCA3.

For the purposes of the present invention, "therapeutically effective amount" refers to the amount of a compound that, when administered to a subject for treating a disease, or disorder, or at least one of the clinical symptoms of a disease or disorder, is sufficient to affect such treatment of the disease, disorder, or symptom. The "therapeutically effective amount" may vary depending, for example, on the compound, the disease, disorder, and/or symptoms of the disease, severity of the disease, disorder, and/or symptoms of the disease, the age, weight, and/or health of the patient to be treated, and the judgment of the prescribing physician. An appropriate amount in any given instance may be readily ascertained by those skilled in the art or capable of determination by routine experimentation. Generally, treatment can be provided for at least several weeks to several years or life-long as needed. In accordance with the methods of the invention, appropriate dosages of SERCA inhibitor can readily be determined by those of ordinary skill in the art of medicine by monitoring the patient for signs of disease amelioration or inhibition, and increasing or decreasing the dosage and/or frequency of treatment as desired.

Where appropriate, a pharmaceutical composition containing a SERCA inhibitor can be administered to a subject suffering from learning or mental disorder along with, or in sequence with, an art-known drug for treating the learning or mental disorder. For example, art-known drugs for treating schizophrenia, include olanzapine, clozapine, haloperidol, and the like. Similarly, a SERCAtrams inhibitor can be used in combination with, or in sequence with, other art-known antipsychotics (e.g., "typical," "atypical," and depot antipsychotics for treating schizophrenia and other psychotic conditions), psychostimulants (for treating attention deficit disorder or learning disorders), or Alzheimer's disease therapeutics (for treating Alzheimer's disease). Such pharmaceutical compositions are included within the invention. In general, the antipsychotic, psychostimulant, or Alzheimer's disease therapeutic typically is administered at a dosage of 0.25-5000 mg/d (e.g., 5-1000 mg/d)). "Typical" antipsychotics are conventional antipsychotics such as phenothiazine, butryophenones, thioxantheses, dibenzoxazepines, dihydroindolones, and diphenylbutylpiperidines. "Atypical" antipsychotics are a new generation of antipsychotics which generally act on the dopamine $D_2$ and $5HT_2$ serotonin receptor and have high levels of efficacy and a benign extrapyramidal symptom side effect profile. Examples of typical antipsychotics include Chlorpromazine, Thioridazine, Mesoridazine, Fluphenazine, Perphenazine, Trifluoperazine, Thiothixene, Haloperidol, Loxapine, Molindone, Acetophenazine, Droperidol, Pimozide. Examples of atypical antipsychotics include Clozapine, Risperidone, Olanzapine, and Quetiapine. Depot antipsychotics also can be used, e.g., Haloperidol decanoate, Fluphenazine decanoate, and Fluphenazine enanthate. Additional antipsychotics include Butaperazine, Carphenazine, Remoxipride, Piperacetazine, Sulpiride, and Ziprasidone. Psychostimulants that are particularly useful for treating attention deficit disorder include Dextroamphetamine, Methamphetamine, Methylphenidate, and Pemoline. Examples of Alzheimer's disease therapeutics that can be used in the invention include Donepezil and Tacrine. Thus, the invention also provides pharmaceutical compositions that contain one or more SERCA2 inhibitors along with an antipsychotic, psychostimulant, or Alzheimer's disease therapeutic.

In addition to, or as an alternative to, conventional methods of diagnosing a subject for a learning disorder or mental disorder, the present invention also embraces a method for diagnosing an increased susceptibility to developing a learning or mental disorder based upon SERCA2 levels. In accordance with the diagnostic method of the invention, a biological sample is obtained from a subject to be tested, and the level of SERCA2 in said sample is measured and compared to a control, wherein an elevated level of SERCA2 as compared to the control indicates an increased susceptibility to developing a learning or mental disorder.

Insofar as SERCA2 is ubiquitous, biological samples in which the level of SERCA2 is to be measured include biopsy samples (e.g., brain tissue) or bodily fluids (e.g., blood). The level of SERCA2 can be determined at the protein level (including amount or activity of SERCA2), wherein the level of SERCA2 as compared to a control is indicative of the level, extent, or severity of disease. For example, a slight increase in SERCA2 as compared to a control is indicative of a mild disease. In particular embodiments, the instant diagnostic assay is carried out my measuring the level or activity of SERCA2 protein. Controls can include relative or absolute amounts of SERCA2 protein or activity levels in a subject or population of subjects without a learning or mental disorder.

In addition to protein analysis and enzymatic analysis, some embodiments embrace genetic analysis, wherein mutations including polymorphisms and DNA modifications (e.g., methylation marks and the like), in the SERCA2 gene are associated with an elevated level of SERCA2 protein or activity and a learning or mental disorder. Such mutations are identified by comparing the nucleotide sequence of the gene encoding SERCA2 in subjects with a learning or mental disorder to the nucleotide sequence of subjects without a learning or mental disorder and establishing a correlation between one or more mutations with an elevated level of SERCA2 protein or activity and the learning or mental disorder.

In addition, the present invention embraces a method for diagnosing a subject suspected of having a learning or mental disorder by measuring the level of synaptic activity of a subject suspected of having a learning or mental disorder, wherein an elevated level of neurotransmitter released from presynaptic terminals as compared to a control subject is indicative of a learning or mental disorder. Levels of synaptic activity can be determined according to the methods exemplified herein or any other method conventionally employed in the art. Subjects serving as controls include those with normal or wild-type levels synaptic activity or a subject with a predetermined amount of synaptic activity.

The diagnostic methods of the invention can be used in the initial determination of whether a subject has a learning or mental disorder or in the confirmation of a diagnosis based upon conventional behavioral or clinical analysis. In this respect, subjects benefiting from the instant diagnostic methods include those suspected of having, or those predisposed (e.g., based upon heredity) to have a learning or mental disorder.

As with the method of treatment, learning or mental disorders that can be diagnosed in accordance with the instant diagnostic methods include, but are not limited to, having, suspected of having or those predisposed to have schizophrenia, Alzheimer's disease, bipolar disorder, schizoaffective disorder, DiGeorge syndrome, attention-deficit hyperactivity disorder, obsessive-compulsive disorder or autism spectrum disorder.

The invention is described in greater detail by the following non-limiting examples.

EXAMPLE 1

Materials and Methods

Animals.

Young (6-8 weeks) and mature (16-20 weeks) Df(16)1/+ male and female mice and their respective gender-controlled wild-type (WT) littermates were used. Mice were maintained on the C57BL/6 genetic background for at least 9 generations.

Brain Slice Preparation.

Acute transverse hippocampal slices (400 μm) were prepared according to known methods (Bayazitov, et al. (2007) *J. Neurosci.* 27:11510-11521). Briefly, mouse brains were quickly removed and placed in cold (4° C.) dissecting artificial cerebrospinal fluid (ACSF) containing 125 mM choline-Cl, 2.5 mM KCl, 0.4 mM $CaCl_2$, 6 mM $MgCl_2$, 1.25 mM $NaH_2PO_4$, 26 mM $NaHCO_3$, and 20 mM glucose (285-295 mOsm), under 95% $O_2$/5% $CO_2$. After dissection, slices were incubated for 1 hour in ACSF containing 125 mM NaCl, 2.5 mM KCl, 2 mM $CaCl_2$, 2 mM $MgCl_2$, 1.25 mM $NaH_2PO_4$, 26 mM $NaHCO_3$, and 10 mM glucose (285-295 mOsm), under 95% $O_2$/5% $CO_2$ at room temperature and then transferred into the submerged recording chamber and superfused (2-3 ml/minute) with warm (30-32° C.) ACSF.

Field Potential Recordings.

The field recordings were performed using a setup with eight submerged recording chambers (Campden Instruments, Lafayette, Ind.). Recordings in each chamber were performed independently. Field excitatory postsynaptic potentials (fEPSPs) from the CA1 stratum radiatum were recorded using an extracellular glass pipette (3-5 MΩ) filled with ACSF. Schaffer collateral fibers in the s. radiatum were stimulated with a bipolar tungsten electrode placed 200 to 300 μm away from the recording pipette. Stimulation intensities were chosen to produce a fEPSP with a 0.5 V/s slope. Paired-pulse facilitation (PPF) experiments were performed using a pair of stimuli of the same intensity delivered 20, 50, 100, 200, and 1000 ms apart.

LTP was induced by three periods of 200-Hz tetanization delivered every 5 minutes. Every period of tetanization was composed of 10 trains of 200-Hz stimulation delivered at the same intensity for 200 ms (40 stimulations) every 5 seconds. A similar protocol has previously been used to induce compound (presynaptic and postsynaptic) LTP at CA3-CA1 synapses in the hippocampus (Zakharenko, et al. (2001) *Nat. Neurosci.* 4:711-7; Cavus & Teyler (1996) *J. Neurophysiol.* 76:3038-47; Zakharenko, et al. (2003) *Neuron* 39:975-90).

Whole-Cell Electrophysiology.

Whole-cell recordings were obtained from the cell bodies of CA1 and CA3 neurons. For current-clamp recordings, patch pipettes (open pipette resistance, 3-5 MO) were filled with an internal solution containing 140 mM $KMeSO_4$, 8 mM NaCl, 1 mM $MgCl_2$, 10 mM HEPES, 5 mM MgATP, 0.4 mM $Na_2$ GTP, 300 μM Fluo 5F, and 10 to 25 μM ALEXA 594 (pH 7.3). For voltage-clamp recordings, the potassium-based solution was replaced with a cesium-based internal solution. Whole-cell recordings were registered using a Multiclamp 700B (Molecular Devices, Sunnyvale, Calif.), digitized (10 kHz; DigiData 1322A, Molecular Devices), and recorded using pCLAMP 9.0 software (Molecular Devices). Spontaneous miniature excitatory postsynaptic currents (mEPSCs)

were recorded at −70 mV holding potential in the presence of picrotoxin (100 μM) and tetrodotoxin (1 μM) in the extracellular solution for at least 1 hour. Amplitude, 10% to 90% rise time, decay time constant, and interevent intervals of mEPSCs were analyzed off-line using the Mini-Analysis Program (Synaptosoft Inc., Leonia, N.J.). All detected events were verified visually, and events with amplitudes less than 5 pA were rejected. Evoked excitatory postsynaptic currents (EPSCs) were recorded in the presence of QX-314 (5 mM) in the intracellular solution to block the generation of back-propagating action potentials (APs) and picrotoxin in the extracellular solution to block inhibitory transmission. EPSCs were evoked at 0.1 Hz with a bipolar electrode placed in the s. radiatum 200 to 300 μm from the recording pipette and 100 to 150 μm from the soma. The amplitude of stimulation was adjusted to evoke 100 pA EPSCs at −70 mV. To determine the average amplitude, rise and decay times, 10 to 20 EPSCs (interstimulus interval >10 seconds) were collected from each neuron. In whole-cell short-term plasticity (STP) experiments, neurons were held at −70 mV, and 10 stimulations at different frequencies were applied to Schaffer collaterals. Data were analyzed by normalizing all EPSCs in the train to the amplitude of the first EPSC. The current ratio of AMPA receptors to NMDA receptors (AMPAR/NMDAR) was calculated from the EPSC traces recorded at +40 mV. The amplitude of stimulation was adjusted to evoke 50 pA EPSCs at −70 mV. The AMPAR current was determined at time points when EPSCs recorded at −70 mV reached their peaks, and the NMDAR currents were determined 100 ms after the peaks. EPSCs were analyzed off-line using Clampfit 10.1 software (Molecular Devices).

Two-Photon Imaging.

Two-photon laser-scanning microscopy (TPLSM) was performed using an Ultima imaging system (Prairie Technologies, Middleton, Wis.), a Ti:sapphire Chameleon Ultra femtosecond-pulsed laser (Coherent Inc., Santa Clara, Calif.), and 60× (0.9 NA) water-immersion IR objectives (Olympus, Center Valley, Pa.). ALEXA FLUOR 594 and Fluo 5F were included in the internal solution and were excited at 820 nm.

ALEXA 594 fluorescence (R, red channel) was used to image and reconstruct dendritic morphology of CA1 neurons and axonal morphology of CA3 neurons. ImageJ was used to analyze dendritic branching and morphology of dendritic spines. Changes in Fluo 5F fluorescence (G, green channel) were used to visualize changes in Ca2+ concentrations in dendritic spines and presynaptic terminals. Synaptically evoked changes in the fluorescence of Fluo 5F were measured in current-clamp using line-scan mode (500 Hz) in dendritic spines. Fluorescence changes were quantified as an increase in Fluo 5F fluorescence normalized to the average ALEXA 594 fluorescence (ΔG/R) (Yasuda R, et al. (2004) *Sci. STKE* 2004:15). To identify synaptic inputs, multiple scans were taken through the apical part of secondary or tertiary dendrites (50-150 μm from a soma) of CA1 neurons in current-clamp mode in response to synaptic stimulation. Stimulation intensity was adjusted to evoke 50 to 100 pA in voltage-clamp mode. Dendritic sites responding with maximal Fluo 5F transients to synaptic stimulation were chosen for imaging, and line scans through corresponding dendritic spines were taken. Calcium transients were measured in a single dendritic site on each recorded neuron. Ca2+ transients in CA3 presynaptic terminals were recorded in a similar fashion. Axons were identified based on ALEXA 594 fluorescence as thin processes emanating from cell bodies, which have no dendritic spines. Presynaptic terminals were identified as boutons situated along axons. Ca2+ transients in presynaptic boutons were recorded in line-scan mode and were evoked by injection of a depolarizing current (0.5 ms, 1.2-2.5 nA) that evoked an AP in the recorded neuron. The number of evoked APs was controlled online in current-clamp mode. Between 2 to 4 boutons were recorded on each neuron and the calcium transients in each bouton were measured independently. When 40 APs at 200 Hz were delivered to a presynaptic bouton, the following precautions were taken: it was monitored that 40 pulses evoked 40 APs in a recorded neuron, and Fluo 5F fluorescence in presynaptic terminals did not saturate. Following delivery of 40 APs at 200 Hz, neurons were depolarized to +20 mV and the Fluo 5F fluorescence in the same bouton was measured. The maximal increase in Fluo 5F fluorescence in presynaptic boutons was 63%±18% higher during +20 mV depolarization than that during 200-Hz tetanization (p=0.03, n=3), indicating that the dye was not saturated during these experiments.

FM 1-43 Assay in Acute Hippocampal Slices.

The FM 1-assay was performed as a modification of a method established in the art (Zakharenko, et al. (2003) *Neuron* 39:975-90; Zakharenko, et al. (2002) *Neuron* 35:1099-1110). FM 1-43 (10 μM) was washed into acute slices for 20 to 30 minutes. Loading of presynaptic boutons was performed by using 10-Hz synaptic stimulation for 2 minutes in the presence of D-APV (50 μM; Tocris Bioscience, Ellisville, Mo.) to avoid synaptic plasticity. ADVASEP-7 (200 μM; Biotium Hayward, Calif.) was then washed in for 20 to 30 minutes to remove the extracellular FM 1-43 dye. Loaded presynaptic boutons were visualized using TPLSM (900 nm). A series of four images at different focal planes was acquired every 5 seconds. Each image was 512×512 pixels (33.6×33.6 μm), 0.066 μm/pixel in the x-y axes, and images were separated by 1-μm steps in the z direction.

Images in each z-section series were aligned and analyzed using custom software written in Interactive Data Language (IDL, ITT Visual Information Solutions, Boulder, Colo.). The area of the slice in which fluorescent puncta were analyzed was restricted to the area within 50 to 150 μm from the pyramidal layer and corresponded to the areas of the apical dendrites where Ca2+ experiments were conducted. Images showing projections of maximal z-axis intensity were made for each subset of a given stack. Puncta were initially identified by a semi-automated procedure written in IDL based on 2 criteria: (1) fluorescence intensity greater than 2× standard deviations above the mean background and (2) diameter between 0.3 to 1.8 μm.

Fluorescence measurements were made by spatially averaging signals over a region centered over each of the identified puncta for each time point during the unloading protocol. Images at successive time points were checked for overlap to help track puncta, which underwent small random movements. Puncta that underwent considerable lateral movement or more than 20% loss of their fluorescent intensity without synaptic stimulation due to photobleaching were excluded from the analysis. The spatially averaged, activity-dependent fluorescence intensity of each punctum obtained at each time point during the unloading procedure was then normalized by the initial fluorescence intensity of that punctum following the FM 1-43-loading procedure prior to unloading. The unloading procedure included 10 trains of tetanic synaptic stimulations (same as the LTP-induction protocol). Each train included 40 stimulations delivered at 200 Hz. This unloading procedure followed by 10-Hz stimulation was applied for 2 minutes to maximally release FM 1-43 from boutons. Decay of intensity during the 200-Hz unloading procedure was fitted to a single exponential function by using a custom-made routine written in IDL, and FM 1-43 destaining half-time (t1/2) for every punctum was calculated. The rate of destaining for each punctum was expressed as 1/t1/2. Puncta for which fluorescence intensities during unloading could not be fitted to a single exponential function were not included in the analysis.

Two-Photon Glutamate Uncaging.

MNI-glutamate (2.5 mM; Tocris Bioscience) was added to the recording ACSF. MNI-glutamate was uncaged by using TriggerSync (Prairie Technologies) and by 0.2- to 0.5-ms pulses that were delivered from a second Ti:sapphire Chameleon Ultra femtosecond-pulsed laser (Coherent Inc.) at 720 nm. The intensity and duration of the uncaging laser was adjusted to mimic mEPSPs (0.4-0.5 mV) or mEPSCs (10-12 pA). In all experiments, before each uncaging pulse, an image of the spine was acquired and automatically aligned with a reference image of the spine. The uncaging laser intensity was normalized to the same degree of ALEXA 594 bleaching by using the previously described method to deliver the same photostimulation power to individual dendritic spines, independent of the depth of the spine in the slice or the refraction index of local tissue (Bloodgood & Sabatini (2005) *Science* 310:866-869). Once the duration and laser power were adjusted, 6 to 9 test pulses were delivered around the perimeter of a spine head to determine the optimal site of uncaging (determined as the maximal response). Another test pulse to the center of the spine head determined the level of ALEXA 594 bleaching. MNI-glutamate was then uncaged at the optimal site. The level of ALEXA 594 bleaching was used to adjust the laser power (but not duration) for other dendritic spines of the same neuron. The point-spread function of the focal volume of two-photon excitation was 300 nm laterally and 1100 nm axially (NA 0.9) based on images of 100-nm fluorescent beads.

Spatial Memory Testing.

Spatial memory was tested in the Morris water maze. A circular steel water maze (diameter, 4 feet; depth, 2 feet) filled with water (room temperature) clouded with white, nontoxic, water-based paint was used. Compass points labeled along the rim served as trial starting positions. For the spatial tasks, water levels were raised 0.25 in above the clear, PLEXI-GLASS escape platform. For the nonspatial task, the water level was lowered so that the escape platform was visible 0.25 inch above the water's surface. The water maze environment was full of visual cues whose locations remained fixed throughout the learning protocol. Mouse movements in the maze were recorded using a video camera tracking system (HVS Image, Co., Buckingham, UK) mounted above the pool, and path length was measured. Animals learned to find a hidden platform in the training (TRA) quadrant using the standard spatial version of the Morris water maze task for successive days. Each day, animals were given four 1-minute trials from each starting position with an intertrial latency of at least 60 seconds. The order of starting locations was counterbalanced each day using a Latin square design.

A spatial memory (probe) trial was administered on the day following the completion of spatial learning. With the platform removed, animals received a single 1-minute trial in which the animal tried to find the escape platform in the TRA quadrant. This trial started from the point that was the farthest from the platform's location on the previous training day. The overall path length was measured for each mouse, and the relative path length for each quadrant was calculated.

Mice started nonspatial learning tasks at least 8 days after completion of the spatial protocol. In this task, the platform was visible above the water's surface. Animals were trained using the standard nonspatial version of the Morris water maze task for 5 successive days. During training day 1, they saw the escape platform located in the same position used during spatial training. Each day thereafter, the escape platform was rotated, in a clockwise manner, to the next quadrant. Each day, animals were given four 1-minute trials in the same manner that occurred during spatial training.

Electron Microscopy.

Hippocampal slices were fixed in 2.5% glutaraldehyde in 0.1 M sodium cacodylate buffer, thrice rinsed in the same buffer, and dehydrated in a graded series of alcohol and then propylene oxide washes. The tissue was infiltrated and embedded in Epon-Araldite and polymerized overnight at 70° C. Seventy-nm sections were cut on a LEICA UC6 ultramicrotome fitted with a Diatome diamond knife and stained with lead citrate and 8% uranyl acetate. Thick sections were trimmed to a region between the CA1 and dentate gyrus cell body layers, and the somata were used as guideposts to find the CA1 area where synapses were identified. The sections were imaged on a JEOL 1200EX11 transmission electron microscope with an AMT XR111 megapixel digital camera. Synapses were counted as regions of membrane enclosing synaptic vesicles in close proximity to a postsynaptic density. Vesicle size and number and postsynaptic density length were measured in ImageJ by tracing with the line or elliptical selection tools followed by measurement.

Quantitative Real-Time PCR.

RNA was isolated from the hippocampi of 4-month-old WT mice and heterozygous Df(16)1/+ littermates (3-5 mice) using the MIRVANA RNA isolation kit (Applied Biosystems, Austin, Tex.). The SUPERSCRIPT III reverse transcriptase kit (Invitrogen, Carlsbad, Calif.) was used to synthesize cDNA from 1 µg RNA. Primers were Gapdh: 5'-GTC GGT GTG AAC GGA TTT G-3' (SEQ ID NO:1) and 5'-TAG ACT CCA CGA CAT ACT CAG CA-3' (SEQ ID NO:2), Tbx1: 5'-GTC ACT GCC TAC CAG AAT CAC-3' (SEQ ID NO:3) and 5'-TCC GAG AGC GAG CAA AGG-3' (SEQ ID NO:4), and Serca2b: 5'-GCC GTT TGT GCT GCT CAT TAT G-3' (SEQ ID NO:5) and 5'-AAC CTC CTT CAC CAG CCA ATA TG-3' (SEQ ID NO:6). Quantitative real-time PCR was conducted using an Applied Biosystems 7900HT Fast Real-time PCR System and the standard protocol (50° C. for 2 minutes, 95° C. for 10 minutes, then 40 cycles of 95° C. for 15 seconds and 60° C. for 1 minute). Standard curves were generated from a reference sample and used to obtain expression levels of each gene. Expression levels of Serca2b and the positive control gene Tbx1, which is contained in the deletion region, were normalized to the housekeeping gene Gapdh for each sample. Samples for each mouse were run in duplicate.

Western Blot Analysis.

Hippocampi were dissected at 4° C. and prepared either as whole-tissue lysates or as crude synaptosomal fractions (P2). Synaptosomes were prepared according to established methods (Gray & Whittaker (1962) *J. Anat.* 96:79-88). In brief, fresh tissue was homogenized in 10 mM HEPES (pH 7.4) and 0.32 M sucrose using a motorized glass-TEFLON homogenizer. To separate the P2 synaptosomal fraction, the homogenate was spun for 5 minutes at 800×g; the supernatant was then centrifuged for 20 minutes at 12,000×g. Tissue or synaptosomal pellets were lysed by freezing and thawing, subsequent syringe passage in ice-cold RIPA buffer (50 mM Tris-HCl (pH 7.4), 1% NP-40, 0.25% sodium deoxycholate, 150 mM NaCl, 1 mM EDTA, and protease inhibitor cocktail tablets (Roche, Indianapolis, Ind.)), and finally brief sonication. The concentrations of protein lysates were determined by BCA assay (Thermo Scientific, Waltham Mass.). A 25-µg sample of each protein extract was electrophoresed on a 10% SDS-PAGE gel, and protein was transferred to PVDF membranes (Invitrogen). The primary antibodies used were goat anti-SERCA2 (1:250; sc-8095, Santa Cruz Biotechnology), mouse anti-β-actin (1:10,000; A5316, Sigma), rabbit anti-synaptophysin (1:1000; Invitrogen), and rabbit anti-NR2A (1:1,000, G9038, Sigma). Blots for synaptophysin and NR2A were probed with HRP-conjugated secondary antibodies and imaged using enhanced chemiluminescence detection by film. SERCA and β-actin western blots were probed with anti-mouse (1:5000) and anti-goat (1:5000) secondary antibodies conjugated to IR dye 680 or 800 (LI-COR Biosciences, Lincoln, Nebr.). These blots were imaged and quantified using the Odyssey infrared imaging system (LI-COR Biosciences). Because this system has a broad linear detection range (10-100,000), the β-actin signal (range, 100-300) did not saturate beyond detection limits, allowing for accurate normalization of SERCA levels to the loading control within the same lane.

Drugs.

Drugs were purchased from Sigma-Aldrich (St. Louis, Mo.), except cyclopiazonic acid (CPA) and thapsigargin, which were purchased from Tocris Bioscience.

Statistics.

All data are represented as mean±standard error of the means. Statistics for all experiments, except behavioral testing studies, were computed using nonparametric Mann-Whitney rank sum and Wilcoxon signed rank tests or t-test measured in Sigma Stat (Systat Software, Inc., Point Richmond, Calif.). Statistics for behavioral testing was computed using repeated measures ANOVA measured in SPSS Statistics (SPSS Inc., Chicago, Ill.).

EXAMPLE 2

Dysregulation of Presynaptic Calcium and Synaptic Plasticity in a Mouse Model of 22q11 Deletion Syndrome Hippocampal LTP is Enhanced in Mature but not in Young Df16(1)/+ Mice.

To examine whether the Df(16)1 deletion affects LTP at excitatory CA3-CA1 synapses, fEPSPs were recorded before and after the delivery of a 200-Hz tetanus to the Schaffer collaterals in acute brain slices from WT and mutant mice. Because this induction protocol potentiates both neurotransmitter release and postsynaptic responses at CA3-CA1 synapses (Bayazitov, et al. (2007) supra; Zakharenko, et al. (2001) Nat. Neurosci. 4:711-7), it was reasoned that it would reveal changes in both presynaptic and postsynaptic components of LTP. Because patients with 22q11DS manifest a decline in cognitive function (Gothelf, et al. (2007) Schizophr. Res. 96:72-81), LTP was teste in mice of two different ages. It was found that LTP was not substantially altered in younger (6-8 weeks) Df(16)1/+ mice compared to WT littermates (p=0.174, 43-45 slices, 8 mice per genotype). In contrast, more mature (16-20 weeks) Df(16)1/+ mice exhibited dramatically enhanced post-tetanic potentiation (PTP) and LTP. The PTP of fEPSPs measured 5 minutes after tetanization (fEPSP5) was approximately 120% higher in mature Df(16)1/+ mice than in WT mice, increasing to 347.9%±35.3% over baseline, as compared to 156%±14.6% in WT littermates (p=0.000002, 24-slices, 6-8 mice). In mature WT mice, LTP of fEPSPs measured 6 hours post-tetanus (fEPSP360) showed a 39.3%±10.5% increase over baseline; whereas in Df(16)1/+ littermates, the fEPSP360 was approximately 200% higher than in WT mice and showed a 118.4%±19.7% increase over baseline (p=0.0005, 24-29 slices, 6-8 mice). Changes in LTP were not due to an increase in the number of stimulated afferents, because no changes in fiber volley were detected in mature Df(16)1/+ or WT mice.

Along with developmental changes in LTP, Df(16)1/+ mice showed age-dependent deficits in the hippocampus-dependent spatial behavioral task, the Morris water maze. Young Df(16)1/+ mice did not show any difference in spatial memory as compared to their WT littermates. However, mature Df(16)1/+ mice showed deficient spatial memory, whereas spatial learning and nonspatial memory remained intact. These results demonstrate that Df(16)1/+ mice develop a deficit in hippocampus-dependent spatial memory that coincides with the onset of LTP abnormalities.

To determine the cause of the substantial increase in LTP in mature Df(16)1/+ mice, differences in basal synaptic transmission were analyzed. However, input-output coupling at CA3-CA1 synapses did not significantly differ between mature Df(16)1/+ mice and WT littermates (p>0.05, 24-29 slices, 6-8 mice). Similarly, single-cell recording revealed no differences in spontaneous or evoked EPSCs in mature Df(16)1/+ mice. Amplitudes of spontaneous miniature EPSCs (mEPSCs) (18.01±1.28 pA for Df(16)1/+ and 17.73±1.03 pA for WT, p=0.87, 6-7 neurons, 551-2445 events per neuron), as well as intervals between mEPSCs (4.78±0.77 seconds for Df1(16)/+ and 3.81±0.74 seconds for WT, p=0.135, 6-7 neurons) were not significantly different between the genotypes. Rise times (2.39±0.11 ms for Df1(16)/+ and 2.47±0.14 ms for WT mice, p=0.29) and decay times (6.38±0.22 ms for Df(16)1/+ and 6.50±0.34 ms for WT mice, p=0.25, 6-7 neurons) of mEPSCs were also not different in mutant and WT mature mice. Similarly, rise times and decay times of EPSCs evoked by a single synaptic stimulation were not significantly different between mature Df(16)1/+ and WT littermates (p=0.29 and 0.49, respectively, 10 neurons per genotype). These data indicate that basal synaptic transmission is normal at excitatory synapses of Df(16)1/+ mice, whereas LTP mechanisms undergo substantial developmental changes in the Df(16)1/+ model of 22q11DS.

Dendritic Morphology and Postsynaptic Function are Preserved in Mature Df16(1)/+Mice.

Previous studies have reported structural abnormalities in the brains of 22q11DS mouse models (Meechan, et al. (2009) Proc. Natl. Acad. Sci. USA 106:16434-16445; Stark, et al. (2008) Nat. Genet. 40:751-760; Mukai, et al. (2008) Nat. Neurosci. 11:1302-1310); thus, it was determined whether developmental changes in synapse structure contribute to the enhanced LTP in mature Df(16)1/+ mice. Dendritic structures were visualized by loading CA1 pyramidal neurons of mature mice with the fluorescent dye ALEXA 594 through a whole-cell pipette and imaging them using TPLSM. The overall morphology of apical dendritic trees of CA1 neurons from mature Df(16)1/+ mice was indistinguishable from that of WT littermates, and quantification of branching by Scholl analysis revealed no difference between genotypes (p=0.863, 7-9 neurons). Furthermore, the length (p=0.21), width (p=0.84) and density (p=0.36) of dendritic spines were similar between mutants and WT littermates (5-7 neurons, 27-28 dendrites, 1171-1290 spines). Electron microscopy was also used to resolve synapses and subsynaptic structures in this region. However, this analysis revealed no abnormalities in the number of CA1 synapses, the number of vesicles, or the size of the postsynaptic densities of mature Df(16)1/+ mice. The only significant change was a slight increase in synaptic vesicle diameter in Df(16)1/+ synapses (30.97±0.27 nm) compared to that of WT synapses (29.18±0.31 nm, 60-80 synapses, p=0.005). However, this change did not affect neurotransmitter release, because the amplitude of spontaneous mEPSCs was not affected in mature Df(16)1/+ mice.

Similarly, electrophysiological characteristics of postsynaptic neurons were not altered in mature Df(16)1/+ mutants. AMPAR/NMDAR ratios measured in CA1 neurons of Df(16) 1/+ and WT mice were not significantly different (p=0.53, 9-11 neurons). There was no difference in the resting membrane potentials (−65.8±0.8 mV for WT and −66.2±1.1 mV for Df(16)1/+ mice, 15 neurons per genotype, p=0.78) or in the excitability of CA1 neurons in mature WT and Df(16)1/+ mice. Injection of depolarizing currents evoked a similar number of APs (p=0.75) at similar threshold membrane potentials (p=0.67, 18-19 neurons) in mutant and WT mice. Thus, these data indicate that morphological or functional changes in postsynaptic CA1 neurons do not contribute to the enhancement of LTP at CA3-CA1 synapses in mature Df1 (16)/+ mice.

Short-Term Synaptic Plasticity is Enhanced in Mature but not Young Df16(1)/+ Mice.

To investigate the presynaptic contribution to the Df(16) 1/+ phenotype, short-term synaptic plasticity, which relies primarily on the presynaptic machinery, was tested. To measure PPF of fEPSPs, field potentials evoked by 2 synaptic stimulations delivered at different interpulse intervals were recorded. It was found that PPF in slices from mature Df(16) 1/+ mice was greater than that of WT littermates (p<0.01, 23-29 slices/6-8 mice). In contrast, PPF in slices from young Df1(16)/+ mice was not elevated compared to that in slices from WT littermates (p>0.05, 18-19 slices/5-6 mice). Using whole-cell recordings in mature animals, EPSC facilitation evoked by trains of synaptic stimulations was measured. Synaptic facilitation during high-frequency stimulation was also substantially enhanced in mature but not young mutant mice. Thus, synaptic facilitation was significantly increased in mature Df(16)1/+ mice compared to WT littermates if induced by a 50-Hz stimulation train (p<0.05, 10-17 neurons) or a 100-Hz (p<0.05, 9-17 neurons) stimulation train. In contrast, no enhancement of synaptic facilitation was observed in younger Df(16)1/+ mice (p>0.05, 6-8 neurons). Thus, both forms of STP were enhanced in mature mutant mice compared to WT littermates, indicating that presynaptic function becomes enhanced in Df1(16)/+ mice upon maturation.

To further distinguish between contributions from presynaptic and postsynaptic loci to the LTP phenotype of mature Df1(16)/+ mice, Ca2+ transients were compared in dendritic spines of CA1 neurons in response to the LTP-induction protocol (40 stimulations at 200 Hz) delivered by either synaptic stimulation (tetanus) or two-photon photolysis of caged glutamate. The comparison of the results from these two methods allows for the distinction between presynaptic and postsynaptic function, because two-photon glutamate uncaging (TGU) releases exogenous glutamate, thereby bypassing the release of endogenous neurotransmitters from presynaptic terminals (Matsuzaki, et al. (2001) *Nat. Neurosci.* 4:1086-1092). To perform these experiments, CA1 neurons were filled with the Ca2+ indicator Fluo 5F and the fluorescent dye ALEXA 595 through a whole-cell pipette and changes in Fluo 5F fluorescence in dendritic spines in current-clamp mode in response to either synaptic stimulation or TGU was measured. To mimic synaptically evoked mEPSPs, the uncaging laser power was adjusted to evoke 0.4- to 0.5-mV EPSPs in response to a single TGU pulse. Ca2+ transients evoked by the 200-Hz tetanus (40 stimulations) were substantially larger in mature Df(16)1/+ mice than in WT mice. On average, during 200-Hz tetanus, peak ΔG/R was 0.16±0.03% in Df(16) 1/+ mice but only 0.10±0.02% in WT mice (p=0.03, 12-15 neurons). In contrast, 200-Hz TGU (40 stimulations) produced Ca2+ transients of similar amplitudes in dendritic spines of Df(16)1/+ and WT mice (p=0.21, 7-11 neurons). Kinetics of postsynaptic Ca2+ transients in response to 40 synaptic or 40 TGU stimulations were similar between Df(16)1/+ and WT mice. Rise times (10%-90%) of Fluo 5F fluorescence changes were 134.4±6.6 ms in Df1(16)1/+ mice and 136.9±12.0 ms in WT mice (12-15 neurons) in response to synaptic stimulation and 168.4±13.9 ms and 153.4±4.2 ms (7-11 neurons), respectively, in response to TGU (p=0.139, one-way ANOVA). Decay times (90%-10%) were 857.4±60.1 ms in Df(16)1/+ mice and 758.3±62.0 ms in WT mice during synaptic stimulation (12-15 neurons) and 907.3±125.1 ms and 895.4±104.5 ms (7-11 neurons), respectively, during TGU (p=0.790, one-way ANOVA). Excitatory postsynaptic potentials evoked by 200 Hz TGU (uEPSPs) in these experiments were also similar between genotypes (p=0.765, 7-11 neurons). Similarly, in voltage-clamp experiments, 40 TGU stimulations delivered at 200 Hz to dendritic spines evoked uEPSCs of similar amplitudes (p=0.257, 5-6 neurons) in Df(16)1/+ and WT mice. In a similar fashion, no differences in amplitudes or kinetics of postsynaptic Ca2+ transients were detected between genotypes in response to a single TGU stimulation. Because no difference in calcium transients were detected between genotypes in TGU experiments, it was determined whether glutamatergic receptors and the calcium indicator were saturated during these experiments. Longer TGU stimulations (80 or 120 pulses) delivered at 200 Hz produced significantly larger calcium transients in dendritic spines than did 40 TGU stimulations (p<0.05, 10 neurons). This result indicated that neither glutamatergic receptors nor the calcium indicator were saturated during the TGU experiments. Together, these findings indicate that the Df(16)1 microdeletion does not affect postsynaptic neurons but enhances neurotransmitter release from presynaptic terminals during high-frequency synaptic activity.

Neurotransmitter Release During Tetanic Stimulation is Increased in Mature Df16(1)/+Mice.

Because previous experiments suggested involvement of enhanced neurotransmitter release in the LTP phenotype in mature Df(16)1/+ mice during high-frequency activity, a more direct method was employed. For this purpose, neurotransmitter release was compared in individual presynaptic boutons using the FM 1-43 dye-unloading assay in acute hippocampal slices. It has been shown that this assay can reliably measure the rate of neurotransmitter release from presynaptic terminals (Zakharenko, et al. (2001) supra; Zakharenko, et al. (2002) supra). Presynaptic CA3 terminals were labeled by electrically stimulating Schaffer collaterals at 10 Hz in the presence of the NMDA receptor blocker D-APV (50 μM) and the fluorescent dye FM 1-43 (10 μM). After washing out the extracellular dye, fluorescent puncta, representing stimulated presynaptic boutons, were observed. A subsequent synaptic stimulation mimicking the LTP-induction protocol and delivered as 10 trains of 40 stimulations at 200 Hz, unloaded the dye from these presynaptic boutons. FM 1-43 destaining from each fluorescent punctum was fitted with a single exponential decay, and destaining rates were calculated. It was found that the average rate of FM 1-43 destaining, which was measured as the reciprocal value of FM 1-43 destaining half-times (1/t1/2) was faster for boutons from Df(16)1/+ mice (0.0562±0.0022 s−1) than for boutons of WT mice (0.0481±0.0019 s−1, n=7 slices for both genotypes, 17-67 boutons per slice, p=0.019). These results confirm that evoked neurotransmitter release, rather than postsynaptic function, is enhanced in the Df(16)1/+ mouse model of 22q11DS.

Presynaptic Calcium Dynamics and SERCA2 Levels are Altered in Mature Df(16)/+Mice.

Evoked neurotransmitter release depends on the concentration of Ca2+ inside presynaptic terminals. To test whether presynaptic Ca2+ is responsible for the observed augmentation of neurotransmitter release, Ca2+ transients were measured in presynaptic terminals of CA3 pyramidal neurons from mature Df(16)1/+ and WT mice. Cells were filled with ALEXA 594 and Fluo 5F, and presynaptic boutons were identified along axons. Axons were distinguished from dendrites by their thinner diameter and the lack of dendritic spines. Calcium transients were detected in individual boutons in response to an AP triggered by injecting a step of depolarizing current through a whole-cell pipette. It was found that a single AP triggered Ca2+ transients of similar amplitudes in presynaptic boutons of mature Df(16)1/+ and WT mice (p=0.66, 34-36 boutons from 10-12 neurons). Rise times (10%-90%) of Ca2+ transients were also indistinguishable between presynaptic boutons of mutant (2.35±0.18 ms, n=34) and WT mice (2.41±0.15 ms, n=36, p=0.78). However, decays of Ca2+ transients (90%-10%) were somewhat slower in boutons of Df(16)1/+ mice (114.26±15.07 ms, n=34) than in WT littermates (73.22±7.34 ms, n=36, p=0.036). This modest alteration in presynaptic Ca2+ kinetics was substantially exacerbated when Ca2+ transients were evoked with the LTP-induction protocol (40 APs delivered at 200 Hz). Similar to the single-AP experiment, the rise of Ca2+ transients showed no detectable difference between the genotypes (rise times (10%-90%), 91.6±2.9 ms and 91.5±2.3 ms, respectively, p=0.79, 40 boutons/15 neurons per genotype). However, the decays (90%-10%) of Ca2+ transients evoked by 40 APs were significantly slower in boutons of mature Df(16)1/+ mice (1491.2±117.5 ms, n=40) than in WT mice (886.1±91.8 ms, n=40, p<0.001). The amplitude of Ca2+ transients evoked by the LTP-induction protocol was also increased in Df(16)1/+ mice. Peak amplitude of Fluo 5F fluorescence evoked by 40 APs in presynaptic terminals of CA3 neurons was approximately 30% higher in Df(16)1/+ mice than in WT littermates (p<0.001, n=40 per genotype). These data indicate a strong dysregulation of Ca2+ dynamics in presynaptic terminals of Df(16)1/+ mutants.

The AP-evoked rise in Ca2+ concentration in presynaptic terminals occurs via activation of voltage-gated Ca2+ channels and is augmented through the release of Ca2+ from internal stores (Emptage, et al. (2001) *Neuron* 29:197-208). The observations that EPSCs evoked by a single synaptic stimulation and that rise times of presynaptic Ca2+ transients are normal in Df(16)1/+ mice strongly argued against the notion that Ca2+ influx through voltage-gated Ca2+ channels is affected in these mutants. Therefore, attention was focused on internal Ca2+ stores, which are filled primarily through SERCA-mediated mechanisms. To test whether the level of SERCA is altered in Df(16)1/+ mice, western blot analysis of hippocampal extracts was used to compare protein levels of SERCA2, the only SERCA isoform expressed in the forebrain (Baba-Aissa, et al. (1998) *Mol. Chem. Neuropathol.* 33:199-208).

Quantification of western blots revealed that the level of SERCA2 protein was increased approximately 20% in whole-tissue lysates of mutant hippocampus compared to that of WT littermates (p=0.006, 9 mice per genotype). This difference was not observed in younger mice (p=0.84, 8-10 mice), indicating that a dysregulation of SERCA expression occurs with an age dependence similar to that of the LTP and spatial memory phenotypes. SERCA2 transcript levels, measured by quantitative real-time PCR, were unaltered, indicating that dysregulation of SERCA2 occurs only at the protein level. This is consistent with results from microarray studies of 22q11DS models, which have shown no alterations in SERCA2 transcript levels (Jurata, et al. (2006) *Schizophr. Res.* 88:251-259; Prescott, et al. (2005) *Hum. Genet.* 116: 486-496; Stark, et al. (2008) supra). Because mature Df(16) 1/+ mice show an enhancement in synaptic plasticity, it was determined whether the level of SERCA2 is increased in the synapses of these mutants. The level of SERCA2 protein was significantly higher in hippocampal synaptosomes of mature Df(16)1/+ mice than in synaptosomes from WT littermates (p<0.001, 8-10 mice).

SERCA2 Inhibitors Rescue Synaptic Phenotypes in Mature Df16(1)/+ Mice.

To test whether SERCA influenced the enhanced neurotransmitter release and LTP in mature Df(16)1/+ mice, the rates of FM 1-43 destaining were measured in the presence of CPA (50 μM), an inhibitor of SERCA pumps that depletes internal Ca2+ stores. The addition of CPA eliminated the difference in FM 1-43 destaining between mature Df(16)1/+ and WT mice. In the presence of CPA, the rate of FM 1-43 destaining in Df(16)1/+ mice elicited with 200-Hz tetanus trains reached 0.0467±0.0026 s−1 (n=10 slices, 21-84 boutons per slice), which was significantly slower than that in the absence of CPA (p=0.02, 7 slices). In contrast, in WT mice the rates of FM 1-43 destaining were similar in the presence (0.0479±0.0027 s−1, n=8 slices, 13-46 boutons per slice) or absence (n=7, p=0.96) of CPA. Interestingly, in the presence of CPA, the rates of FM 1-43 destaining from presynaptic boutons in Df(16)1/+ and WT mice did not differ (p=0.76); thus, CPA rescued enhanced neurotransmitter release in Df(16)1/+ mice. No significant difference in decay (p=0.22) or amplitude (p=0.72) of presynaptic Ca2+ transients evoked by 40 APs (200 Hz) was also found in the presence of CPA in WT and Df(16)1/+ mice (14-19 boutons, 5 neurons per genotype). These data indicate that blocking SERCA with CPA rescued presynaptic calcium dysregulation in mutant mice. In a similar fashion, CPA rescued the increase in PPF in Df(16) 1/+ mice. Thus, PPF measured at 20- and 50-ms intervals in Df(16)1/+ mice was significantly reduced from 2.09±0.15 and 2.01±0.09, respectively, in the absence of CPA to 1.78±0.13 (p=0.001, 28 slices) and 1.76±0.09 (p=0.019, 28 slices) when CPA was added to the bath solution. In contrast, in WT mice PPF was similar in the presence (1.64±0.11 for 20-ms and 1.61±0.05 for 50-ms intervals, 19 slices) and in the absence of CPA (1.58±0.08 for 20-ms, p=0.49 and 1.69±0.05 for 50-ms intervals, p=0.62, 19 slices). Importantly, no significant difference in PPF was found between the genotypes in the presence of CPA (p=0.283 for 20-ms interval and p=0.455 for the 50-ms interval, 19-28 slices). Together, these data indicate that the depletion of internal Ca2+ stores rescued the enhancement of presynaptic Ca2+ transients and neurotransmitter release in mature Df(16)1/+ mice. They also predict that the depletion of Ca2+ stores by SERCA inhibitors should rescue the LTP enhancement in mature Df(16)1/+ mice.

To test this, LTP induced by 200-Hz tetanization was measured in the presence of either CPA or thapsigargin (4 μm), another SERCA inhibitor. Both agents rescued the enhancement of PTP and LTP in Df(16)1/+ mice. In slices from CPA-treated Df(16)1/+ mice, fEPSP5 was reduced to 45% (p=0.0001), and fEPSP360 was reduced to 60% of that detected in vehicle-treated Df(16)1/+ mice (p=0.021, 16-23 slices, 7-8 mice). Similarly, thapsigargin reduced the fEPSP5 and fEPSP360 in slices from Df(16)1/+ mice to 69% (p=0.015) and 57% (p=0.005), respectively, of that in vehicle-treated Df(16)1/+ slices (22-23 slices, 8-10 mice). Interestingly, neither SERCA inhibitor affected WT LTP induced by the 200-Hz induction protocol. This is consistent with results showing that SERCA inhibitors affect LTP induced only by weak (but not strong, e.g., 200 Hz) stimulation protocols (Behnisch & Reymann KG (1995) *Neurosci. Lett.* 192:185-188; Matias, et al. (2002) *Neuroreport* 13:2577-2580; Zhang, et al. (2009) *Nature* 460:632-636). Thus, in the presence of CPA, WT fEPSP5 (p=0.210) and fEPSP360 (p=0.680) were not significantly different from those seen in the absence of CPA (16-52 slices, 6-15 mice). Similarly, no significant difference was seen between fEPSP5 (p=0.384) and fEPSP360 (p=0.939) in the presence or absence of thapsigargin (22-52 slices, 10-mice). Importantly, in the presence of CPA and thapsigargin, the increases in fEPSPs at either time point were not significantly different between mature Df(16)1/+ and WT mice (p=0.951 and p=0.436 for fEPSP5, and p=0.297 and p=0.623 for fEPSP360, respectively), indicating that inhibition of SERCA rescued the LTP phenotype in Df(16)1/+ mice.

The results herein demonstrate that within 16 to 20 weeks of birth the Df(16)1/+ mouse model of 22q11DS develops a substantial enhancement in LTP that coincides with a deficit in spatial memory. Furthermore, the increase in LTP caused by the hemizygous deletion of 22q11DS-related genes is due to enhanced glutamate release from presynaptic terminals and not due to changes in postsynaptic structures or function. Moreover, it was demonstrated that SERCA2 upregulation is a contributor to the dysregulation of presynaptic Ca2+, enhanced glutamate release, and increased LTP in the model of 22q11DS.

What is claimed is:

1. A method for treating a schizophrenia comprising administering to a subject that has been diagnosed with schizophrenia a therapeutically effective amount of a sarco (endo)plasmic reticulum calcium ATPase type 2 (SERCA2) inhibitor, wherein said SERCA2 inhibitor is cyclopiazonic acid or analog thereof so that the activity of SERCA2 in the brain cells of the subject is inhibited, thereby treating the subject's schizophrenia.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
gtcggtgtga acggatttg                                                  19

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
tagactccac gacatactca gca                                             23

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
gtcactgcct accagaatca c                                               21

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
tccgagagcg agcaaagg                                                   18

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 5
gccgtttgtg ctgctcatta tg                                    22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
aacctccttc accagccaat atg                                   23
```